US010683303B2

(12) United States Patent
Assink et al.

(10) Patent No.: US 10,683,303 B2
(45) Date of Patent: Jun. 16, 2020

(54) PROCESSES FOR PRODUCING METHENAMINE MANDELATE

(71) Applicant: Albemarle Corporation, Charlotte, NC (US)

(72) Inventors: Bryce Kelly Assink, Kalamazoo, MI (US); Tino Jon Caviggiola, III, Zeeland, MI (US)

(73) Assignee: ALBEMARLE CORPORATION, Charlotte, NC (US)

(*) Notice: Subject to any disclaimer, the term of this patent is extended or adjusted under 35 U.S.C. 154(b) by 0 days.

(21) Appl. No.: 16/306,719

(22) PCT Filed: May 26, 2017

(86) PCT No.: PCT/US2017/034742
§ 371 (c)(1),
(2) Date: Dec. 3, 2018

(87) PCT Pub. No.: WO2017/210122
PCT Pub. Date: Dec. 7, 2017

(65) Prior Publication Data
US 2019/0127388 A1 May 2, 2019

Related U.S. Application Data

(60) Provisional application No. 62/345,440, filed on Jun. 3, 2016.

(51) Int. Cl.
C07D 487/18 (2006.01)
C07C 51/41 (2006.01)
C07D 487/22 (2006.01)
C07B 43/04 (2006.01)

(52) U.S. Cl.
CPC ............ C07D 487/22 (2013.01); C07B 43/04 (2013.01); C07C 51/41 (2013.01); C07C 51/412 (2013.01); C07D 487/18 (2013.01)

(58) Field of Classification Search
CPC .................................................... C07D 487/18
USPC ................................................. 544/185, 186
See application file for complete search history.

(56) References Cited

U.S. PATENT DOCUMENTS

| 1,566,820 A | 12/1925 | Carter |
| 2,124,321 A | 7/1938 | Tisza |
| 2,449,040 A | 9/1948 | Schideler et al. |
| 2,542,315 A | 2/1951 | Eickmeyer |
| 2,640,826 A | 6/1953 | MacLean et al. |
| 2,762,800 A | 9/1953 | Meissner et al. |
| 2,762,799 A | 9/1956 | Meissner et al. |
| 3,061,608 A | 10/1962 | Millikan |
| 3,288,790 A | 11/1966 | Lefebvre et al. |
| 4,001,231 A | 1/1977 | Diamond |

FOREIGN PATENT DOCUMENTS

| DE | 824055 | 12/1951 |
| DE | 824056 | 12/1951 |
| DE | 57854 | 9/1967 |
| DE | 10103770 A1 | 8/2002 |
| GB | 512583 | 9/1939 |

OTHER PUBLICATIONS

DS 10103770, Aug. 1, 2002;English Translation form EPO site, Sep. 13, 2019.*
DE 824056, Oct. 12, 1951; English Translation form EPO site, Sep. 13, 2019.*
DE 824055, Oct. 12, 1951; English Translation form EPO site, Sep. 13, 2019.*
Meissner et al., Industrial & Engineering Chemistry, 40(4), 724-727,, 1954.*
International Search Report and Written Opinion of corresponding international application No. PCT/US2017/034742 dated Jul. 28, 2017, all enclosed pages cited.
International Preliminary Report on Patentability of corresponding international application No. PCT/US2017/034742 dated Dec. 4, 2018, all enclosed pages cited.

* cited by examiner

Primary Examiner — Venkataraman Balasubramanian
(74) Attorney, Agent, or Firm — Troy S. Kleckley

(57) ABSTRACT

Processes are provided for the production of methenamine mandelate that do not require the isolation of produced methenamine prior to production of the methenamine mandelate.

6 Claims, 1 Drawing Sheet

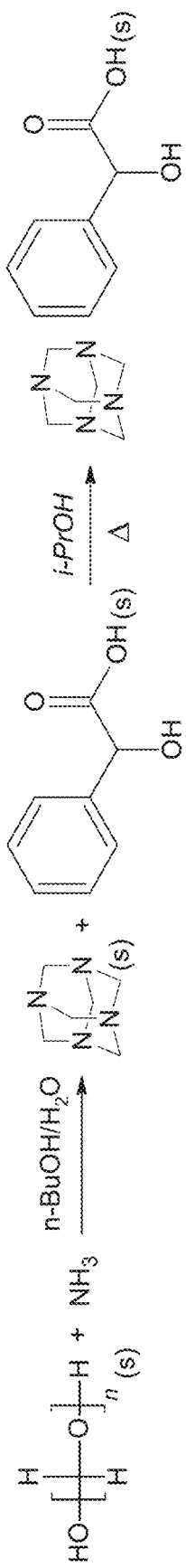

PROCESSES FOR PRODUCING METHENAMINE MANDELATE

CROSS-REFERENCE TO RELATED APPLICATIONS

This application, filed Dec. 3, 2018, is a national entry under 35 U.S.C. § 371 of and claims the benefit of Patent Cooperation Treaty Application No. PCT/US2017/034742, which claims priority to and the benefit of U.S. Provisional Application 62/345,440, filed Jun. 3, 2016, the entire contents and substance of all of which are hereby incorporated by reference as if fully set forth below.

BACKGROUND

Methenamine mandelate is useful for the treatment of urinary tract infections. In known processes for producing methenamine mandelate, methenamine that has been produced and isolated is combined with mandelic acid. See, e.g., U.S. Pat. No. 4,001,231.

In order to more efficiently and cost-effectively produce methenamine mandelate, there is a need for processes that do not require the isolation of produced methenamine prior to production of the methenamine mandelate.

THE INVENTION

This invention meets the above-described needs by providing processes that comprise: bubbling ammonia through a first combination comprising at least paraformaldehyde, a first $C_2$-$C_6$ alcohol, and water, while maintaining the first combination at about 20 deg. C. to about 90 deg. C., thereby producing a first reaction product comprising methenamine; combining at least the first reaction product, mandelic acid, and a second $C_2$-$C_6$ alcohol under heat, thereby producing a second reaction product; heating the second reaction product to a temperature of about 20 deg. C. to about 100 deg. C.; and cooling the second reaction product to at least about 70 deg. C., thereby producing a composition comprising methenamine mandelate.

FIGURES

Processes of this invention will be better understood by reference to the FIG. 1 in which a scheme according to this invention is illustrated.

DETAILED DESCRIPTION

Processes of this invention comprise bubbling ammonia through a first combination comprising at least paraformaldehyde, a first $C_2$-$C_6$ alcohol, and water, while maintaining the first combination at about 20 deg. C. to about 90 deg. C., or about 20 deg. C. to about 60 deg. C., or about 20 deg. C. to about 40 deg. C., thereby producing a first reaction product comprising methenamine. The first $C_2$-$C_6$ alcohol can include, for example, alcohols such as n-butanol, cyclohexanol, n-propanol, isopropanol, n-pentanol, n-hexanol, isobutanol, s-butanol, or t-butanol. The ammonia can be bubbled through the first combination at least until the first combination substantially ceases to absorb the ammonia. The first reaction product can also comprise water, and can have a water content.

Processes of this invention can also comprise using techniques know to those skilled in the art to reduce the water content of the first reaction product. For example, water can be removed by azeodistillation. In one example, the first reaction product can be brought to reflux, first $C_2$-$C_6$ alcohol and water vapor condensed, and the bottom water layer removed while the condensed first $C_2$-$C_6$ alcohol is returned to the first reaction product. After water removal by azeodistillation is no longer practical, a portion of the remaining first $C_2$-$C_6$ alcohol can be removed by distillation, which helps remove additional water. Additionally, if the water content is above the desired amount, e.g., above 0.2 wt %, additional first $C_2$-$C_6$ alcohol can be charged to the first reaction product and then distilled off again in order to lower the water content. The water content of the first reaction product, once reduced, can be from about 0 wt % to about 2 wt %, or from about 0 wt % to about 0.2 wt %, or from more than 0 wt % to about 2 wt %, or from more than 0 wt % to about 0.2 wt %.

Processes of this invention also comprise combining at least the first reaction product, mandelic acid, and a second $C_2$-$C_6$ alcohol under heat, thereby producing a second reaction product. The second $C_2$-$C_6$ alcohol can include, for example, alcohols such as isopropanol, n-butanol, cyclohexanol, n-propanol, isopropanol, n-pentanol, n-hexanol, isobutanol, s-butanol, or t-butanol. The mandelic acid can be dissolved in the second $C_2$-$C_6$ alcohol. The combining can take place under heat sufficient to produce a second reaction product.

Processes of this invention also comprise heating the second reaction product to a temperature of about 20 deg. C. to about 100 deg. C., or about 20 deg. C. to about 90 deg. C., or about 50 deg. C. to about 90 deg. C., or about 80 deg. C. to about 90 deg. C.

Processes of this invention also comprise cooling the second reaction product to at least about 70 deg. C., or to at least about 50 deg. C., or to at least about 30 deg. C., thereby producing a composition comprising methenamine mandelate. The cooling can take place over a period of about 90 to about 140 minutes.

EXAMPLES

The following examples are illustrative of the principles of this invention. It is understood that this invention is not limited to any one specific embodiment exemplified herein, whether in the examples or the remainder of this patent application.

Example 1

A 2-L round-bottomed flask was equipped with a Dean-Stark trap, a condenser, and a thermocouple. Paraformaldehyde (203.7 g, 6.78 mol, 6 eq.), n-butanol (610 mL, 3.00 mL/g), and water (68 mL, 0.33 mL/g) were charged and stirred at 0 to 25° C. Ammonia gas (77 g, 77 mL) was bubbled in sub-surface at a rate of about 0.6 ml/min, which minimized ammonia loss through the bubbler The exotherm associated with the ammonia addition was controlled at 20 to 60° C. with a water bath. When the reaction mixture did not absorb any more ammonia at 51° C., the reaction was deemed complete. The reaction mixture was then heated to reflux and water (186.4 g) was removed azeotropically with the Dean-Stark trap. The water content of the concentrated mixture was measured by Karl Fischer titration with a target of <0.2%. Mandelic acid (172.0 g, 1.13 mol) was dissolved in isopropanol (520 mL) in a separate flask. The mandelic acid solution was filtered and charged to the reaction mixture with an isopropanol rinse (50 mL). The reaction mixture was heated to 90° C. to dissolve all solids and allowed to cool slowly to affect precipitation of the product. The reaction slurry was allowed to cool from 70-30° C. over approximately 120 minutes. At approximately 25° C. the solid was collected by vacuum filtration and washed with isopropanol (97 mL). The wetcake was dried overnight under vacuum, at 60° C., with a slight nitrogen bleed, to produce 250.7 g of methenamine mandelate as a white solid.

Example 2

A 500 mL, 4-neck round bottom flask was charged with paraformaldehyde (60 g), n-butanol (120 mL), and water (20 mL). The slurry was charged with ammonia while maintaining a temperature below 40° C. Upon addition of the ammonia, the reaction solution was warmed to 65-85° C. and held for ≥30 minutes. The resulting solution was warmed to reflux and water was removed by means of azeodistillation. Butanol was then removed by distillation. The water content of the reaction mixture was measured by Karl Fischer titration and was found to be 0.08 wt % H2O. A solution of mandelic acid (48.4 g) in isopropyl alcohol (145 mL) was then added to the reaction slurry and the resulting mixture was warmed to 80-90° C. and held until dissolution of solids occurred. The solution was then cooled to 22-30° C. and the resulting solid was isolated by vacuum filtration and washed with isopropyl alcohol (93 mL). The solid was dried under vacuum, at 60-65° C., overnight with a slight N2 purge, to produce 81.87 g of methenamine mandelate as a white solid, an uncorrected yield of 88.0%.

Processes of this invention are advantageous in that such processes allow for the direct formation of methenamine mandelate without isolation of the methenamine reactant. Also, such processes can be run in a single reactor and require only one isolation step. Processes of this invention have the added advantage of using solid paraformaldehyde, thus avoiding the use of gaseous formaldehyde, which is a known carcinogen.

It is to be understood that the reactants and components referred to by chemical name or formula anywhere in the specification or claims hereof, whether referred to in the singular or plural, are identified as they exist prior to being combined with or coming into contact with another substance referred to by chemical name or chemical type (e.g., another reactant, a solvent, or etc.). It matters not what chemical changes, transformations and/or reactions, if any, take place in the resulting combination or solution or reaction medium as such changes, transformations and/or reactions are the natural result of bringing the specified reactants and/or components together under the conditions called for pursuant to this disclosure. Thus the reactants and components are identified as ingredients to be brought together in connection with performing a desired chemical reaction or in forming a combination to be used in conducting a desired reaction. Accordingly, even though the claims hereinafter may refer to substances, components and/or ingredients in the present tense ("comprises", "is", etc.), the reference is to the substance, component or ingredient as it existed at the time just before it was first contacted, combined, blended or mixed with one or more other substances, components and/or ingredients in accordance with the present disclosure. Whatever transformations, if any, which occur in situ as a reaction is conducted, is what the claim is intended to cover. Thus the fact that a substance, component or ingredient may have lost its original identity through a chemical reaction or transformation during the course of contacting, combining, blending or mixing operations, if conducted in accordance with this disclosure and with the application of common sense and the ordinary skill of a chemist, is thus wholly immaterial for an accurate understanding and appreciation of the true meaning and substance of this disclosure and the claims thereof. As will be familiar to those skilled in the art, the terms "combined", "combining", and the like as used herein mean that the components that are "combined" or that one is "combining" are put into a container with each other. Likewise a "combination" of components means the components having been put together in a container.

While the present invention has been described in terms of one or more preferred embodiments, it is to be understood that other modifications may be made without departing from the scope of the invention, which is set forth in the claims below.

What is claimed is:

1. A process comprising:
bubbling ammonia through a first combination comprising paraformaldehyde, a first C2-C6 alcohol, and water, while maintaining the first combination at about 20 deg. C. to about 90 deg. C., thereby producing a first reaction product comprising methenamine;
combining at least the first reaction product, mandelic acid, and a second C2-C6 alcohol under heat, thereby producing a second reaction product;
heating the second reaction product to a temperature of about 20 deg. C. to about 100 deg. C.; and
cooling the second reaction product to at least about 70 deg. C.,
thereby producing a composition comprising methenamine mandelate.

2. A process as in claim 1 wherein the first C2-C6 alcohol comprises n-butanol, cyclohexanol, n-propanol, isopropanol, n-pentanol, n-hexanol, isobutanol, s-butanol, or t-butanol.

3. A process as in claim 1 wherein the second C2-C6 alcohol comprises as isopropanol, n-butanol, cyclohexanol, n-propanol, isopropanol, n-pentanol, n-hexanol, isobutanol, s-butanol, or t-butanol.

4. A composition comprising methenamine mandelate, wherein the methenamine mandelate is prepared by a process comprising:
bubbling ammonia through a first combination comprising paraformaldehyde, a first C2-C6 alcohol, and water, while maintaining the first combination at about 20 deg. C. to about 90 deg. C., thereby producing a first reaction product comprising methenamine;
combining at least the first reaction product, mandelic acid, and a second C2-C6 alcohol under heat, thereby producing a second reaction product;
heating the second reaction product to a temperature of about 20 deg. C. to about 100 deg. C.; and
cooling the second reaction product to at least about 70 deg. C.,
thereby producing a composition comprising methenamine mandelate.

5. The composition of claim 1, wherein the first C2-C6 alcohol comprises n-butanol, cyclohexanol, n-propanol, isopropanol, n-pentanol, n-hexanol, isobutanol, s-butanol, or t-butanol.

6. The composition of claim 1, wherein the second C2-C6 alcohol comprises as isopropanol, n-butanol, cyclohexanol, n-propanol, isopropanol, n-pentanol, n-hexanol, isobutanol, s-butanol, or t-butanol.

* * * * *